(12) United States Patent
Herman

(10) Patent No.: US 11,079,756 B2
(45) Date of Patent: Aug. 3, 2021

(54) MONITORING OF STEERING WHEEL ENGAGEMENT FOR AUTONOMOUS VEHICLES

(71) Applicant: Ford Global Technologies, LLC, Dearborn, MI (US)

(72) Inventor: David Michael Herman, Oak Park, MI (US)

(73) Assignee: FORD GLOBAL TECHNOLOGIES, LLC, Dearborn, MI (US)

( * ) Notice: Subject to any disclaimer, the term of this patent is extended or adjusted under 35 U.S.C. 154(b) by 295 days.

(21) Appl. No.: 16/294,541

(22) Filed: Mar. 6, 2019

(65) Prior Publication Data
US 2020/0285231 A1 Sep. 10, 2020

(51) Int. Cl.
*G05D 1/00* (2006.01)
*A61B 5/00* (2006.01)
(Continued)

(52) U.S. Cl.
CPC ......... *G05D 1/0055* (2013.01); *A61B 5/0077* (2013.01); *A61B 5/01* (2013.01); *A61B 5/0245* (2013.01); *A61B 5/6893* (2013.01); *A61B 5/6898* (2013.01); *A61B 5/7246* (2013.01); *B60Q 9/00* (2013.01); *B60W 50/14* (2013.01); *G05D 1/0088* (2013.01); *A61B 2503/12* (2013.01); *B60N 2/002* (2013.01);
(Continued)

(58) Field of Classification Search
CPC .. G05D 1/00; G08B 23/00; A61B 5/18; A61B 5/00; B60K 28/063
See application file for complete search history.

(56) References Cited

U.S. PATENT DOCUMENTS

| | | | | |
|---|---|---|---|---|
| 4,706,072 A | * | 11/1987 | Ikeyama | B60K 28/063 340/575 |
| 2011/0234413 A1 | * | 9/2011 | Dobbs | G08B 21/06 340/575 |
| 2016/0302730 A1 | * | 10/2016 | Odate | A61B 5/00 |

FOREIGN PATENT DOCUMENTS

| | | | | |
|---|---|---|---|---|
| CN | 202960535 U | * | 6/2013 | ............... A61B 5/18 |
| DE | 102014117824 A1 | | 6/2016 | |

(Continued)

OTHER PUBLICATIONS

Guha Balakrishnan et al. *Detecting Pulse from Head Motions in Video*, 2013, 8 pages.

(Continued)

*Primary Examiner* — Yuri Kan
(74) *Attorney, Agent, or Firm* — Frank A. MacKenzie; Bejin Bieneman PLC

(57) ABSTRACT

Method and apparatus are disclosed for monitoring of steering wheel engagement for autonomous vehicles. An example vehicle includes an autonomy unit configured to perform autonomous motive functions, a steering wheel, capacitive sensors coupled to the steering wheel, a second sensor configured to monitor an operator, and a controller. The controller is configured to detect a first heart rate via the capacitive sensors, detect a second heart rate via the second sensor, identify that an engagement-imitating device is coupled to the steering wheel responsive to determining that the first heart rate does not correlate with the second heart rate, and emit an alert responsive to determining that the engagement-imitating device is coupled to the steering wheel.

20 Claims, 6 Drawing Sheets

(51) Int. Cl.
    *G08B 23/00*     (2006.01)
    *A61B 5/18*     (2006.01)
    *A61B 5/01*     (2006.01)
    *B60Q 9/00*     (2006.01)
    *B60W 50/14*     (2020.01)
    *A61B 5/0245*     (2006.01)
    *B60N 2/00*     (2006.01)

(52) U.S. Cl.
    CPC . *B60W 2050/143* (2013.01); *B60W 2050/146* (2013.01); *B60W 2420/42* (2013.01); *B60W 2540/22* (2013.01)

(56) References Cited

FOREIGN PATENT DOCUMENTS

| | | |
|---|---|---|
| FR | 3028341 A1 | 5/2016 |
| JP | 2016203660 A | 12/2016 |

OTHER PUBLICATIONS

Magdalena Lewandowska et al., *Measuring Pulse Rate with a Webcam—a Non-contact Method for Evaluating Cardiac Activity*, 2011, 6 pages.

Xiaobai Li et al., *Remote Heart Rate Measurement From Face Videos Under Realistic Situations*, 2014, 8 pages.

\* cited by examiner

MONITORING OF STEERING WHEEL ENGAGEMENT FOR AUTONOMOUS VEHICLES

TECHNICAL FIELD

The present disclosure generally relates to steering wheels and, more specifically, to monitoring of steering wheel engagement for autonomous vehicles.

BACKGROUND

Many vehicles include functions in which motive functions are autonomously controlled by the vehicle. For instance, some vehicles include autonomous systems that control acceleration, deceleration, braking, steering, and/or other motive functions of the vehicle. Typically, a vehicle with an autonomous or semi-autonomous system includes sensors that collect information of a surrounding environment of the vehicle. In such instances, the autonomous system performs motive functions based on, at least in part, the collected information. Such systems may encounter a situation for which manual intervention is required and, thus, a human driver must remain alert and capable of taking over the vehicle's motive functions.

SUMMARY

The appended claims define this application. The present disclosure summarizes aspects of the embodiments and should not be used to limit the claims. Other implementations are contemplated in accordance with the techniques described herein, as will be apparent to one having ordinary skill in the art upon examination of the following drawings and detailed description, and these implementations are intended to be within the scope of this application.

Example embodiments are shown for monitoring of steering wheel engagement for autonomous vehicles. An example disclosed vehicle includes an autonomy unit configured to perform or semi-autonomous autonomous motive functions, a steering wheel, capacitive sensors coupled to the steering wheel, a second sensor configured to monitor an operator, and a controller. The controller is configured to detect a first heart rate via the capacitive sensors, detect a second heart rate via the second sensor, identify that an engagement-imitating device is coupled to the steering wheel responsive to determining that the first heart rate does not correlate with the second heart rate, and emit an alert responsive to determining that the engagement-imitating device is coupled to the steering wheel.

In some examples, the autonomy unit is configured to autonomously decelerate the vehicle responsive to the controller identifying that the engagement-imitating device is coupled to the steering wheel. In some examples, the controller is configured to disable the autonomy unit responsive to the controller identifying that the engagement-imitating device is coupled to the steering wheel.

In some examples, the controller is configured to identify that the operator is holding the steering wheel responsive to determining that the first heart rate correlates with the second heart rate. In some examples, the controller is configured to enable the autonomy unit to perform the autonomous motive functions responsive to the controller identifying that the operator is holding the steering wheel without the engagement-imitating device being coupled to the steering wheel.

In some examples, the controller is configured to identify that the operator is not holding the steering wheel when the controller does not detect the first heart rate and the second heart rate. In some such examples, responsive to identifying that the operator is not holding the steering wheel, the controller is configured to at least one of emit an alert, disable the autonomy unit, and decelerate the vehicle via the autonomy unit.

Some examples further include a display. In such examples, the alert includes a visual alert and the controller is configured to emit the visual alert via the display. Some examples further include a speaker. In such examples, the alert includes an audio alert and the controller is configured to emit the audio alert via the speaker. Further, in some examples, the alert includes a visual alert.

Some examples further include a third sensor for monitoring a third heart rate of the operator. In some such examples, the controller is configured to identify that the engagement-imitating device is coupled to the steering wheel responsive to determining that the third heart rate does not correlate with at least one of the first heart rate and the second heart rate. In some such examples, the third sensor includes at least one of a seat occupancy sensor, a seatbelt sensor, a thermometer, and a capacitive touchscreen.

Some examples further include a communication module configured to collect a third heart rate from a mobile device of the operator. In some such examples, the controller is configured to identify that the engagement-imitating device is coupled to the steering wheel responsive to determining that the third heart rate does not correlate with at least one of the first heart rate and the second heart rate.

In some examples, the second sensor includes a camera (e.g., a near infrared camera).

In some examples, to detect the first heart rate, one or more of the capacitive sensors is configured to collect measurements when the operator touches the steering wheel and the controller is configured to detect a rate at which the measurements spike and that corresponds with a heart rate of the operator. In some examples, to detect the second heart rate, the controller is configured to detect a characteristic that corresponds with a heart rate of the operator within images of the operator captured by the second sensor.

In some examples, the controller is configured to determine that the first heart rate does not correlate with the second heart rate in response to determining that a difference between the first heart rate and the second heart rate is greater than a predefined threshold. In some examples, the controller is configured to normalize, filter, and align the first heart rate and the second heart rate prior to comparing the first heart rate and the second heart rate.

An example disclosed method for an autonomous vehicle system includes detecting a first heart rate for an operator of a vehicle via capacitive sensors coupled to a steering wheel of the vehicle and detecting a second heart rate for the operator via a camera of the vehicle. The example disclosed system also includes comparing, via a processor, the first heart rate and the second heart rate and identifying, via the processor, that an engagement-imitating device is coupled to the steering wheel responsive to determining that the first heart rate does not correlate with the second heart rate. The example disclosed system also includes emitting an alert responsive to determining that the engagement-imitating device is coupled to the steering wheel.

BRIEF DESCRIPTION OF THE DRAWINGS

For a better understanding of the invention, reference may be made to embodiments shown in the following drawings.

The components in the drawings are not necessarily to scale and related elements may be omitted, or in some instances proportions may have been exaggerated, so as to emphasize and clearly illustrate the novel features described herein. In addition, system components can be variously arranged, as known in the art. Further, in the drawings, like reference numerals designate corresponding parts throughout the several views.

DETAILED DESCRIPTION OF EXAMPLE EMBODIMENTS

Figure 1:
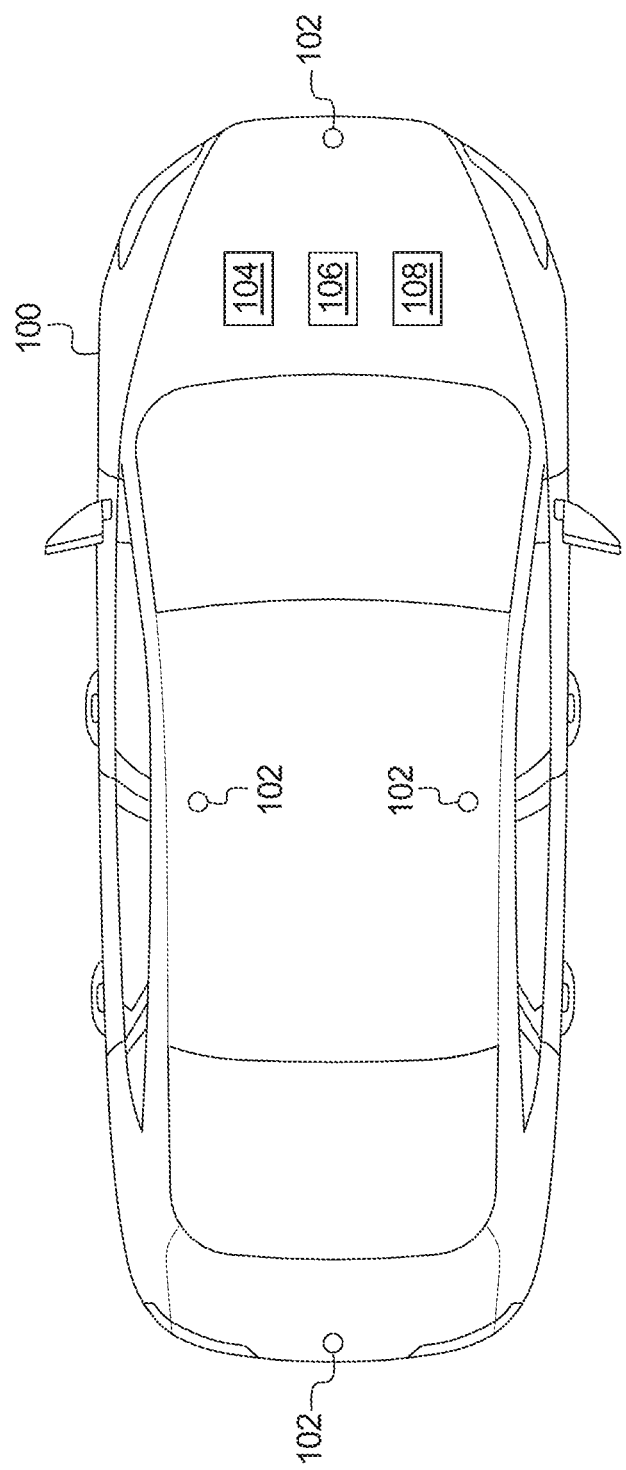
FIG. 1 illustrates an example vehicle in accordance with the teachings herein.

While the invention may be embodied in various forms, there are shown in the drawings, and will hereinafter be described, some exemplary and non-limiting embodiments, with the understanding that the present disclosure is to be considered an exemplification of the invention and is not intended to limit the invention to the specific embodiments illustrated.

Many vehicles include functions in which motive functions are autonomously controlled by the vehicle. For instance, some vehicles include autonomous systems that control acceleration, deceleration, braking, steering, and/or other motive functions of the vehicle. Typically, a vehicle with an autonomous or semi-autonomous system includes sensors that collect information of a surrounding environment of the vehicle. In such instances, the autonomous system performs motive functions based on, at least in part, the collected information.

Some governmental agencies, such as the National Highway Traffic Safety Administration (NHTSA) of the United States Department of Transportation (DoT), require an operator of a vehicle to hold a steering wheel while an autonomous system of the vehicle is operating the vehicle as a safety measure to enable the operator to quickly perform a manual takeover of the vehicle if necessary. In turn, many autonomous vehicles are configured to monitor whether the operator is holding the steering wheel when an autonomous system is performing motive functions for the vehicle. For instance, autonomous vehicles may include torque sensors within a steering wheel to monitor for a torque that corresponds with an operator holding a steering wheel. In other instances, autonomous vehicles may include capacitive sensors within a steering wheel to monitor for a capacitance that corresponds with an operator holding a steering wheel. Some operators of autonomous vehicles have found this requirement to be bothersome and have used engagement-imitating devices to potentially circumvent such user-engagement confirmation features. In turn, such operators potentially may be less capable of quickly resuming manual operation if necessary.

As used herein, an "engagement-imitating device" and an "operator-attentiveness bypass device" refer to a device that is configured to couple to a steering wheel to mimic an operator holding and/or otherwise interacting with a steering wheel. Some engagement-imitating devices may include a weight that applies a small torque to a steering wheel having torque sensor(s) in an attempt to mimic an operator holding a steering wheel. Other engagement-imitating devices may include a battery that emits a charge to a steering wheel having capacitive sensor(s) in an attempt to mimic an operator holding a steering wheel. Some such engagement-imitating devices may vary the charge emitted by the battery in a fixed pattern to resemble a human heart beat.

Example methods and apparatus disclosed herein include a user-engagement confirmation feature for an autonomous vehicle that is configured to determine whether an operator is holding a steering wheel of the autonomous vehicle by monitoring for a heart rate of the operator via capacitive and/or other sensors located on the steering wheel of the vehicle. Further, example, the user-engagement confirmation feature of methods and apparatus disclosed herein is configured to detect whether an engagement-imitating device that mimics a heart rate is coupled to the steering wheel by comparing the heart rate measured by the capacitive and/or other sensors of the steering wheel to a heart rate measured by other sensor device(s). Examples disclosed herein include a controller that determines (1) a first measured and offset heart rate based on data collected by the capacitive and/or other sensors of the steering wheel and (2) a second measured and offset heart rate based on the data collected by the other sensor device(s) (e.g., a camera, a mobile device such as a wearable, a seat occupancy sensor, a seatbelt sensor, a thermometer, a capacitive touchscreen, etc.). If the measured heart rates correlate with each other, the controller determines that the operator is holding the steering wheel and subsequently permits autonomous functions to be performed. If the measured heart rates do not correlate with each other, the controller determines that an engagement-imitating device is being used and subsequently performs a corresponding corrective measure (or that another passenger is holding the steering wheel). If the measured heart rates are unable to be detected, the controller determines that neither the operator nor an engagement-imitating device is in contact with the steering wheel and subsequently performs a corresponding corrective measure. Example corrective measures include emitting an alert, autonomously decelerating the vehicle, temporarily deactivating autonomous system(s) of the vehicle, etc.

Turning to the figures, FIG. 1 illustrates an example vehicle 100 in accordance with the teachings herein. The vehicle 100 may be a standard gasoline powered vehicle, a hybrid vehicle, an electric vehicle, a fuel cell vehicle, and/or any other mobility implement type of vehicle. The vehicle 100 includes parts related to mobility, such as a powertrain with an engine, a transmission, a suspension, a driveshaft, and/or wheels, etc. The vehicle 100 may be semi-autonomous (e.g., some routine motive functions are controllable controlled by the vehicle 100) or autonomous (e.g., all motive functions are controllable by the vehicle 100 without direct driver input).

In the illustrated example, the vehicle 100 includes range-detection sensors 102. As used herein, a "range-detection sensor" refers to an electronic device that is configured to collect information to detect a presence of and distance to nearby object(s). In the illustrated example, the range-detection sensors 102 include proximity sensors and/or cameras. The proximity sensors are configured to detect the presence, proximity, and/or location of object(s) near the vehicle 100. For example, the proximity sensors include radar sensor(s), lidar sensor(s), ultrasonic sensor(s), and/or any other sensor configured to detect the presence, proximity, and/or location of nearby object(s). A radar sensor detects and locates an object via radio waves, a lidar sensor detects and locates the object via lasers, and an ultrasonic sensor detects and locates the object via ultrasound waves. Further, the cameras are configured to capture image(s) and/or video of a surrounding area of the vehicle 100 to enable nearby object(s) to be identified and located. In the illustrated example, the range-detection sensors 102 are located on each side (e.g., front, rear, left, right) along the vehicle 100 to enable the range-detection sensors 102 to monitor a surrounding area of the vehicle 100. In other examples, one or more of the range-detection sensors 102 are positioned at any other location on the vehicle 100 that enables the range-detection sensors 102 to monitor the surrounding area of the vehicle 100.

The vehicle 100 of the illustrated example also includes a communication module 104 that includes wireless network interfaces to enable communication with other devices (e.g., a mobile device of an operator 204 of FIG. 2) and/or external networks. The communication module 104 also includes hardware (e.g., processors, memory, antenna, etc.) and software to control the wireless network interfaces. For example, the communication module 104 includes hardware and software to wirelessly communicate with a mobile device (e.g., a smart phone, a wearable, a smart watch, etc.) via a wireless personal area network (WPAN) and/or a wireless local area network (WLAN). In some examples, the communication module 104 implements the Bluetooth® and/or Bluetooth® Low Energy (BLE) protocols. The Bluetooth® and BLE protocols are set forth in Volume 6 of the Bluetooth® Specification 4.0 (and subsequent revisions) maintained by the Bluetooth® Special Interest Group. Additionally or alternatively, the communication module 104 is configured to wirelessly communicate via Wi-Fi®, Near Field Communication (NFC), ultra-wide band (UWB) communication, ultra-high frequency (UHF) communication, low frequency (LF) communication, and/or any other communication protocol(s) that enable the communication module 104 to communicatively couple to a nearby mobile device. Further, in some examples, the communication module 104 includes hardware and software to communicate with external network(s). For example, the external network(s) may be a public network, such as the Internet; a private network, such as an intranet; or combinations thereof, and may utilize a variety of networking protocols now available or later developed including, but not limited to, TCP/IP-based networking protocols. For example, the communication module 104 is configured for cellular networks, such as Global System for Mobile Communications (GSM), Universal Mobile Telecommunications System (UMTS), Long Term Evolution (LTE), Code Division Multiple Access (CDMA), etc.

In the illustrated example, the vehicle 100 also includes an autonomy unit 106. The autonomy unit 106 is an electronic control unit that is configured to perform autonomous and/or semi-autonomous motive functions for the vehicle 100. For example, the autonomy unit 106 is configured to autonomously control performance of driving maneuvers of the vehicle 100 based upon, at least in part, data collected by the range-detection sensors 102. In the illustrated example, the autonomy unit 106 is configured to control performance of driving maneuvers for a fully autonomous system. Further, the autonomy unit 106 is configured to control performance of driving maneuvers for a fully autonomous system, such as adaptive cruise control, collision avoidance, lane-assist (e.g., lane centering), etc.

Further, the vehicle 100 of the illustrated example includes a user-engagement controller 108. In the illustrated example, the user-engagement controller 108 is configured to monitor the engagement of a steering wheel of the vehicle 100 (e.g., a steering wheel 300 of FIG. 3). For example, some governmental agencies, such as the NHTSA, require an operator of the vehicle 100 (e.g., the operator 204 of FIG. 2) hold the steering wheel while the autonomy unit 106 is autonomously operating the vehicle 100 to enable the operator to quickly perform a manual takeover of the vehicle 100 if necessary. Further, in some instances, an operator is permitted to remove his or her hands from a steering wheel in certain instances (e.g., in a highway setting) and is required to place his or her hands on the steering wheel in other instances (e.g., when challenging road conditions are present). In turn, the user-engagement controller 108 of the illustrated example is configured to monitor the steering wheel and/or operator of the vehicle 100 to determine whether the operator of the vehicle 100 is holding the steering wheel while the autonomy unit 106 is performing an autonomous system. For example, the user-engagement controller 108 is configured to detect when (1) an operator of the vehicle (e.g., an operator 204 of FIG. 2) is holding the steering wheel, (2) the operator is not holding the steering wheel, and/or (3) an engagement-imitating device (e.g., an engagement-imitating device 400 of FIG. 4) is coupled to the steering wheel.

Further, the user-engagement controller 108 is configured to initiate vehicle function(s) based on the engagement monitoring of the steering wheel. For example, in response to identifying that (1) an engagement-imitating device is coupled to the steering wheel and/or (2) the operator is not holding the steering wheel, the user-engagement controller 108 is configured to (a) emit an alert (e.g., an audio, visual, and/or haptic alert), (b) instruct the autonomy unit 106 to autonomously decelerate the vehicle 100, and/or (c) temporarily disable the autonomy unit 106 until the engagement-imitating device is removed from the steering wheel. For example, the user-engagement controller 108 is configured to emit (1) an audio alert via a display (e.g., a display 206 of FIG. 2), (2) an audio alert via speakers (e.g., speakers 622 of FIG. 6), and/or (3) a haptic alert via haptic device(s) located in the steering wheel and/or a seat (e.g., a seat 202 of FIG. 2). The user-engagement controller 108 of the illustrated example also is configured to enable the autonomy unit 106 to autonomously perform motive functions in response to identifying that the operator is holding the steering wheel without an engagement-imitating device being coupled to the steering wheel.

Figure 2:
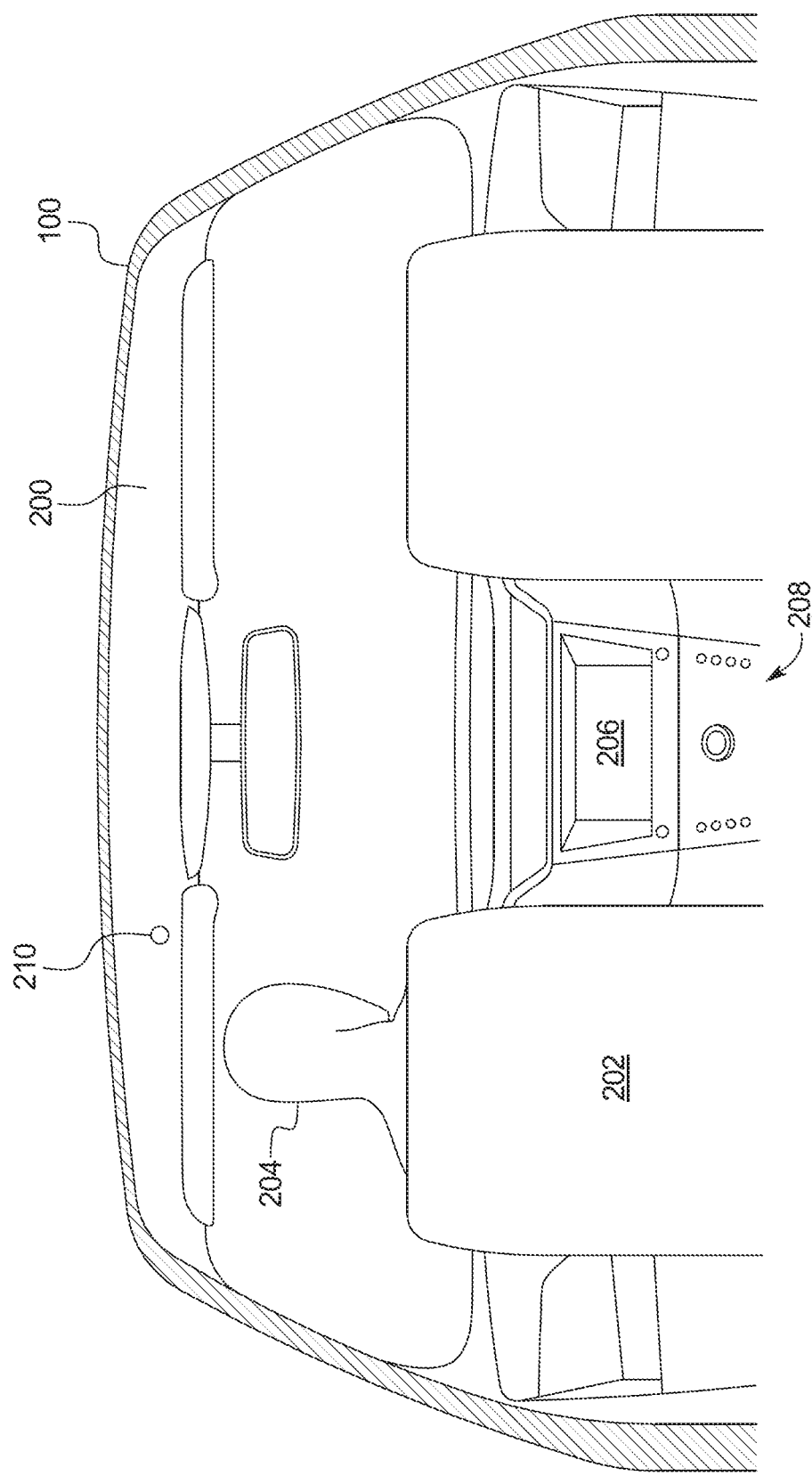
FIG. 2 illustrates a cabin of the vehicle of FIG. 1.

FIG. 2 illustrates a cabin 200 of the vehicle 100. As illustrated in FIG. 2, a seat 202 (e.g., a driver's seat) is positioned within the cabin 200 on which an operator 204 of the vehicle 100 is to sit while operating the vehicle 100. Further, a display 206 and console input devices 208 are located within the cabin 200 of the vehicle 100. For example, the display 206 and the console input devices 208 are located on a dashboard, a center console, and/or another console of the vehicle 100 that is adjacent to the seat 202 within the cabin 200 to facilitate the operator 204 in utilizing the display 206 and the console input devices 208.

In the illustrated example, the console input devices 208 include input device(s), such as switches, buttons, etc., that enable the operator 204 and/or a passenger to control various features of the vehicle 100. Further, the display 206 of the illustrated example includes a center console display, such as a liquid crystal display (LCD), an organic light emitting diode (OLED) display, a flat panel display, a solid state display, etc. Additionally or alternatively, the display 206 includes a heads-up display that is configured to project an image onto a windshield and/or other surface of the vehicle 100. In the illustrated example, the display 206 is configured to emit a visual alert to the operator 204 in response to the user-engagement controller 108 determining that the operator 204 is not holding a steering wheel (e.g., the steering wheel 300 of FIG. 3) of the vehicle 100 (e.g., when an engagement-imitating device is coupled to the steering wheel). In some examples, the display 206 includes a touchscreen that is configured to receive input information from the operator 204 and/or other user. Further, in some examples, the console input devices 208 are configured to receive input information that corresponds with output information being presented via the display 206.

Further, a camera 210 is located within the cabin 200 of the vehicle 100. The camera 210 is configured to monitor the operator 204. In the illustrated example, the camera 210 is located on a ceiling of the cabin 200 adjacent to the seat 202 of the operator 204. In other examples, the camera 210 is located at any other position that enables the camera 210 to monitor the operator 204. Further, in some examples, the vehicle 100 includes a plurality of cameras (e.g., including the camera 210) that arranged and configured to monitor the operator 204. In some examples, the camera 210 is operatively coupled to lighting (e.g., a near infrared (NIR) light emitting diode (LED)) for illumination and/or active lighting to facilitate the camera 210 in capturing data (e.g., measuring depth via structured lighting, phase shift methods, other time-of-flight methods, etc.).

In the illustrated example, the camera 210 of the illustrated example is positioned and oriented to capture image(s) of the operator 204 for monitoring the operator 204. For example, the camera 210 is positioned and oriented to capture image(s) of a face of the operator 204 that enable the user-engagement controller 108 to measure a heart rate of the operator 204. That is, the user-engagement controller 108 is configured to measure a heart rate of the operator 204 by detecting a characteristic within the image(s) captured by the camera 210 that correlates with the heart rate of the operator 204. Examples of such characteristics include head oscillations caused by cardiovascular oscillation, a blood volume pulse of micro-vascular blood vessels, a body temperature, color-based characteristics of the operator 204, etc. In some examples, the camera includes a visible-light camera, an infrared camera, a near infrared (NIR) camera, a time-of-flight camera, a thermal camera, etc.

Figure 3:
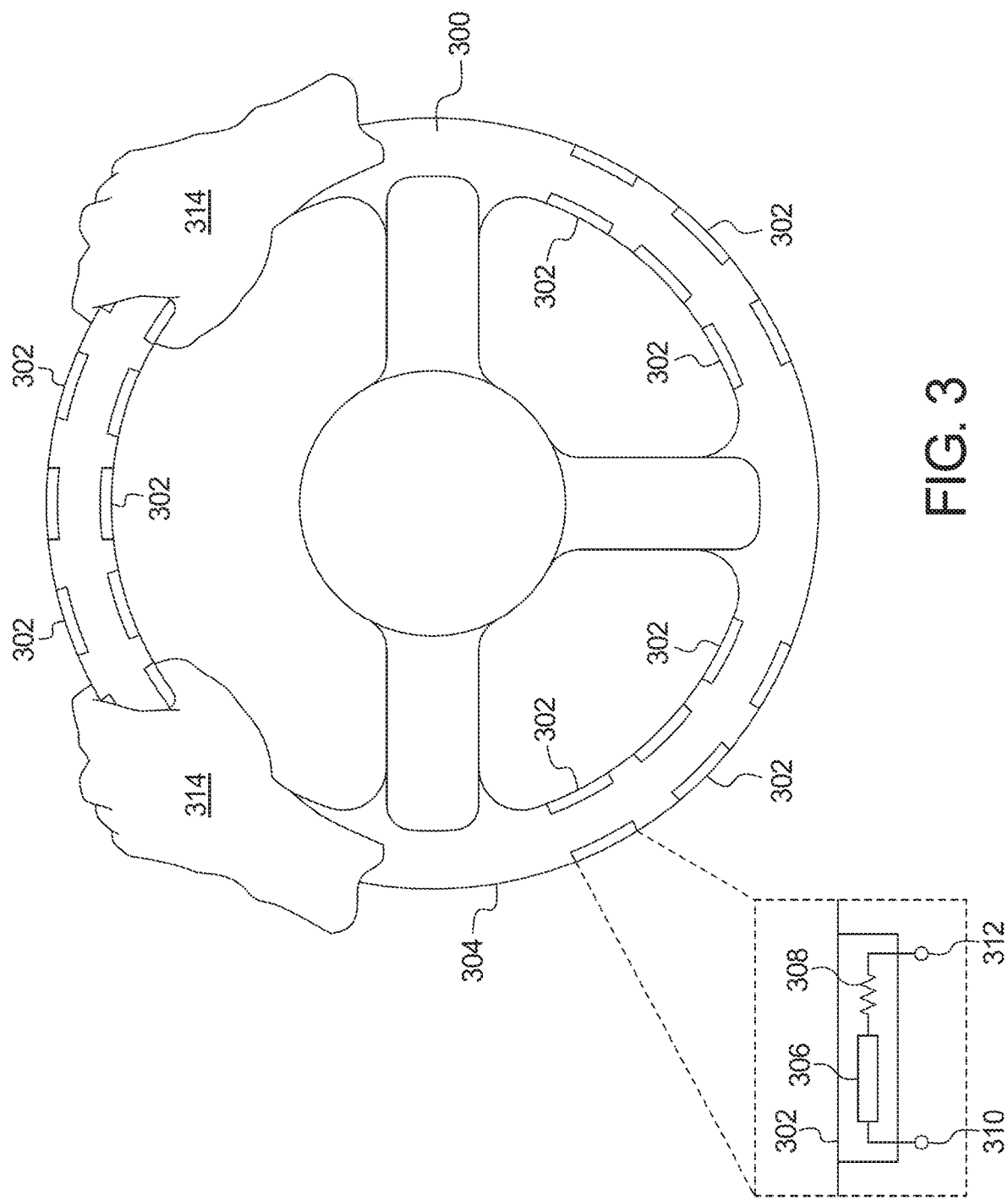
FIG. 3 illustrates a steering wheel of the vehicle of FIG. 1.

FIG. 3 illustrates a steering wheel 300 of the vehicle 100. In the illustrated example, the steering wheel 300 includes a plurality of capacitive sensors 302 configured to monitor for hands 314 of the operator 204 and/or an engagement-imitating device (e.g., an engagement-imitating device 400 of FIG. 4). Additionally or alternatively, the steering wheel 300 includes a plurality of other sensors, such as torque sensors, that are also configured to monitor for the hands 314 of the operator 204 and/or the engagement-imitating device. Further, in some examples, the steering wheel 300 includes one or more input devices, such as a button, a switch, and/or a touchscreen, that the operator 204 is to engage to indicate that the operator 204 is holding and/or otherwise interacting with the steering wheel 300.

In the illustrated example, the capacitive sensors 302 are located along an exterior surface 304 of the steering wheel 300. In some examples, the capacitive sensors 302 are embedded in an inner and/or outer perimeter of the steering wheel 300. In some examples, the capacitive sensors 302 are embedded in a front and/or back portion of the steering wheel 300. In some examples, the capacitive sensors 302 are flush with an outer surface of the steering wheel 300. Further, in some examples, the capacitive sensors 302 are covered in a non-conductive material (e.g., fabric such as nylon, rubber, or PVC, etc.).

In the illustrated example, each of the capacitive sensors 302 includes a capacitive plate 306, a resistive element 308, a signal terminal 310, and a measurement terminal 312. The capacitance of the capacitive plate 306 increases when a part of the hand of the driver is proximate to the corresponding one of the capacitive sensors 302. Further, the signal terminal 310 and the measurement terminal 312 are electrically coupled to a variable voltage source to enable a change in capacitance to be measured. That is, each of the capacitive sensors 302 is configured to collect measurements to identify when the operator 204 is touching the steering wheel 300. Further, in the illustrated example, each of the capacitive sensors 302 has a measurement sensitivity that enables the detection of a heart rate of the operator 204 when the operator 204 is holding the steering wheel 300. For example, each of the capacitive sensors 302 is configured to detect spikes or drops in the capacitive measurements that correspond with the heart rate of the operator 204. The user-engagement controller 108 is configured to identify a heart rate of the operator 204 by measuring the time between each of the spikes or drops in the capacitive measurements.

Figure 4:
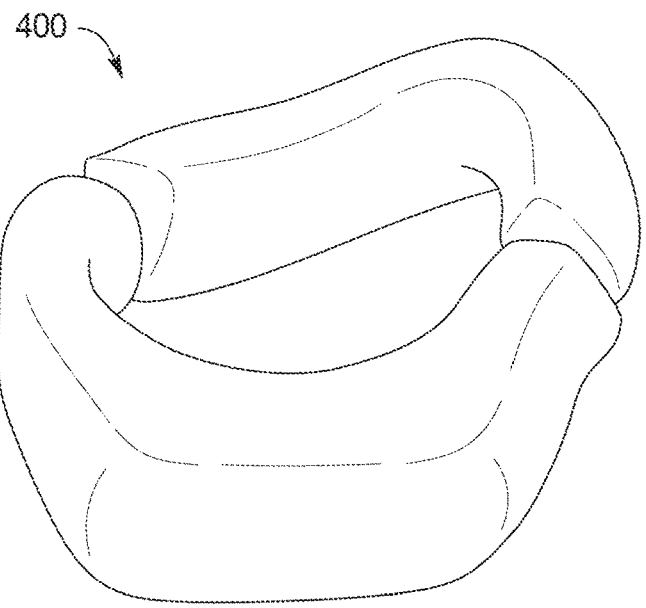
FIG. 4 depicts an engagement-imitating device for the steering wheel of FIG. 3.
Figure 5:
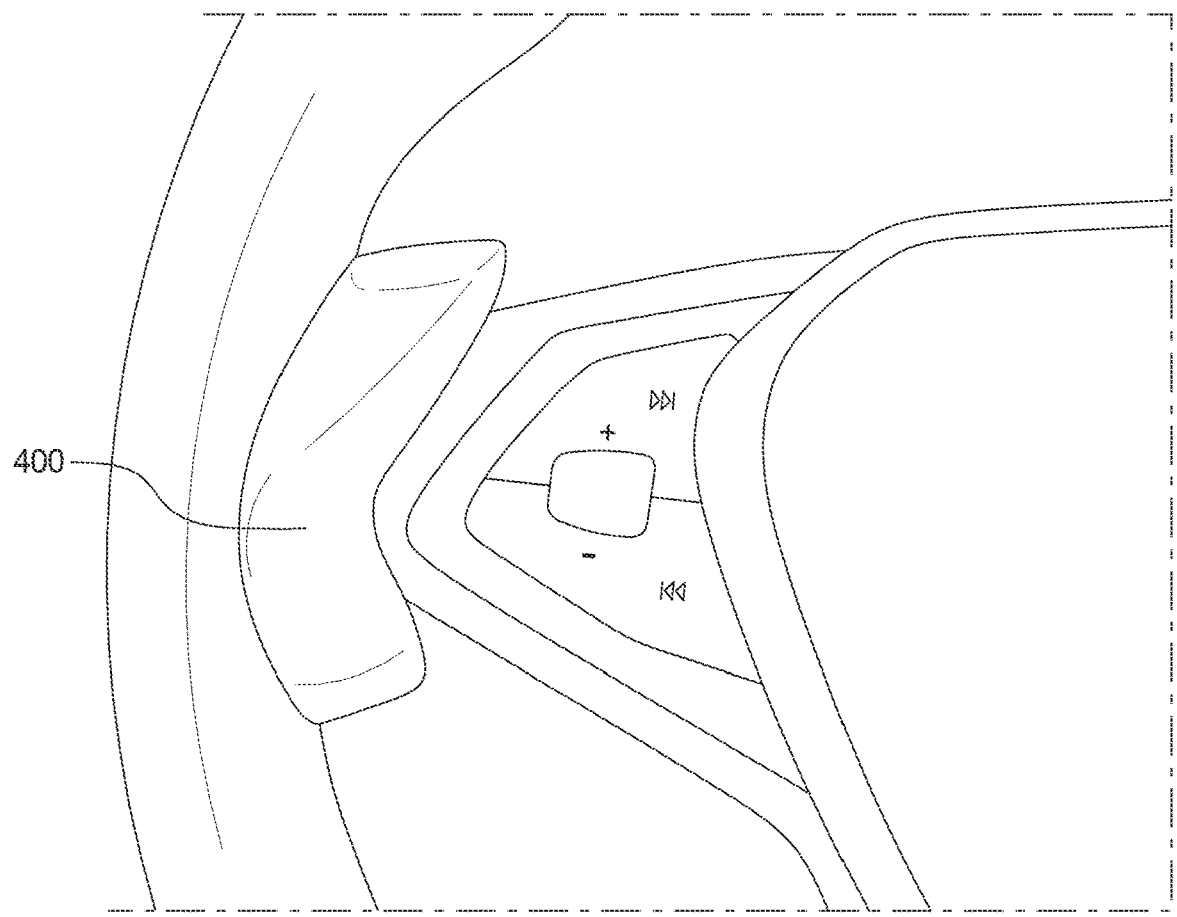
FIG. 5 illustrates the engagement-imitating device of FIG. 4 coupled to the steering wheel of FIG. 3.

FIGS. 4 depict an engagement-imitating device 400 for the steering wheel 300. More specifically, FIG. 4 illustrates the engagement-imitating device 400 uncoupled from the steering wheel 300, and FIG. 5 illustrates the engagement-imitating device 400 coupled to the steering wheel 300. When coupled to the steering wheel 300, the engagement-imitating device 400 may trick a user-engagement confirmation feature of an autonomous system of the vehicle 100 by mimicking the operator 204 holding the steering wheel 300. In some examples, the engagement-imitating device 400 includes a weight that applies a small torque and/or other force (e.g., a time-variant force associated with a heartbeat) to the steering wheel 300 that may mimic the operator 204 holding the steering wheel 300. In some examples, the engagement-imitating device 400 includes a battery that emits a charge that may mimic the capacitance (e.g., a time-variant capacitance associated with a heartbeat) of the operator 204 holding the steering wheel 300. Governmental agencies, such as the NHTSA, have prohibited the use of such devices (e.g., the Autopilot Buddy® produced by Dolder, Falco and Reese Partners LLC) to ensure that operators of autonomous and/or semi-autonomous vehicles are properly engaged while motive functions are being autonomously performed.

In operation, the user-engagement controller 108 is configured to detect a first measured heart rate via one or more of the capacitive sensors 302 and a second measured heart rate via the camera 210 and/or other sensor(s) (e.g., a seat occupancy sensor, a seatbelt sensor, a thermometer, a mobile device such as a wearable, a capacitive touchscreen of the display 206 and/or other display, etc.). The user-engagement controller 108 is configured to compare the measured heart rates to determine whether they correlate with each other.

In some examples, the user-engagement controller 108 is configured to normalize and/or filter the first measured heart rate and/or the second measured heart rate prior to comparing the first and second measured heart rates. Additionally or alternatively, the user-engagement controller 108 is configured to align the first and second measured heart rates with each other prior to comparing the first and second measured heart rates. In some examples, the user-engagement controller 108 is configured to utilize a correlation method, such as Pearson correlation and/or Spearmen correlation, to determine whether the measured heart rates correlate with each other. Further, in some examples, the user-engagement controller 108 is configured to determine that the measured heart rates do not correlate with each other in response to determining that a difference between the measured heart rates is greater than a predefined threshold. For example, if the correlation is less than the predefined threshold (e.g., a minimum p-value or Bayesian posterior probability), the user-engagement controller 108 is configured to determine that the measured heart rates do not correlate with each other. In contrast, if the correlation is greater than or equal to the predefined threshold, the user-engagement controller 108 is configured to determine that the measured heart rates do correlate with each other.

In response to determining that the first measured heart rate and the second measured heart rate correlate with each other, the user-engagement controller 108 is configured to identify that the operator 204 is holding the steering wheel 300. In turn, upon identifying that the operator 204 is holding the steering wheel 300, the user-engagement controller 108 is configured to enable the autonomy unit 106 to perform motive function(s) for an autonomous system of the vehicle. In response to determining that the first measured heart rate and the second measured heart rate do not correlate with each other, the user-engagement controller 108 is configured to identify that the engagement-imitating device 400 is coupled to the steering wheel 300. In turn, the user-engagement controller 108 is configured to perform a corrective measure, such as emit an alert (e.g., an audio, visual, and/or haptic alert), cause the autonomy unit 106 to decelerate the vehicle 100, temporarily disable the autonomy unit 106, etc. Further, in response to determining that the first measured heart rate and the second measured heart rate have not been detected, the user-engagement controller 108 is configured to identify that the operator 204 is holding and the engagement-imitating device 400 is not coupled to the steering wheel 300. In turn, the user-engagement controller 108 is configured to perform a corrective measure, such as emit an alert, cause the autonomy unit 106 to decelerate the vehicle 100, temporarily disable the autonomy unit 106, etc.

In some examples, the user-engagement controller 108 is configured to further monitor the operator 204 utilizing data from another sensor (e.g., a seat occupancy sensor, a seatbelt sensor, a thermometer, a mobile device such as a wearable, a capacitive touchscreen of the display 206, etc.). For example, the other sensor includes a sensor of a mobile device, such as a wearable, in communication with the communication module 104 of the vehicle 100. The user-engagement controller 108 also is configured to determine a third measured heart rate based on the data of the other sensor. In other examples, the user-engagement controller 108 is configured to collect the third measured heart rate from the mobile device. For example, some mobile devices, such as wearables, are able to measure heart rates of users based on collected data.

Further, in such examples, the user-engagement controller 108 is configured to determine the third measured heart rate to the other measured heart rates to determine whether the operator 204 is holding the steering wheel 300, the operator 204 is not holding the steering wheel 300, and/or the engagement-imitating device 400 is coupled to the steering wheel 300. For example, the user-engagement controller 108 is configured to identify that the operator 204 is holding the steering wheel 300 if all of the measured heart rates correlate with each other. The user-engagement controller 108 is configured to identify that the engagement-imitating device 400 is coupled to the steering wheel 300 if one or more of the measured heart rates does not match the other measured heart rates. For example, the engagement-imitating device 400 detects the presence of the engagement-imitating device 400 if the first measured heart rate that was determined based on the capacitive sensors 302 does not correlate with the other measured heart rates.

Figure 6:
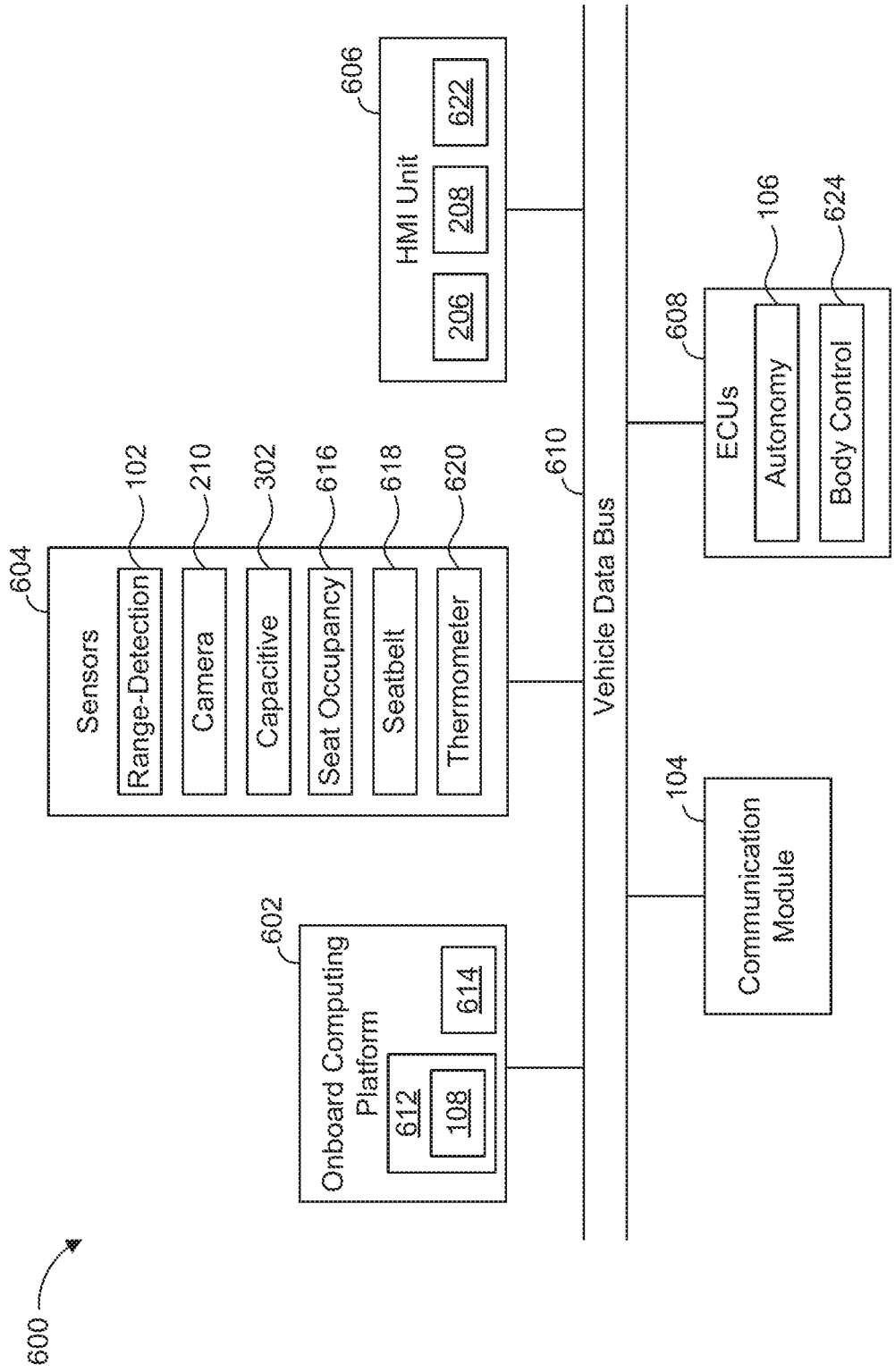
FIG. 6 is a block diagram of electronic components of the vehicle of FIG. 1.

FIG. 6 is a block diagram of electronic components 600 of the vehicle 100. In the illustrated example, the electronic components 600 include an onboard computing platform 602, sensors 604, a human-machine interface (HMI) unit 606, the communication module 104, electronic control units (ECUs) 608, and a vehicle data bus 610.

The onboard computing platform 602 includes a processor 612 (also referred to as a microcontroller unit and a controller) and memory 614. In the illustrated example, the processor 612 of the onboard computing platform 602 is structured to include the user-engagement controller 108. In other examples, the user-engagement controller 108 is incorporated into another ECU with its own processor and memory. The processor 612 may be any suitable processing device or set of processing devices such as, but not limited to, a microprocessor, a microcontroller-based platform, an integrated circuit, one or more field programmable gate arrays (FPGAs), and/or one or more application-specific integrated circuits (ASICs). The memory 614 may be volatile memory (e.g., RAM including non-volatile RAM, magnetic RAM, ferroelectric RAM, etc.), non-volatile memory (e.g., disk memory, FLASH memory, EPROMs, EEPROMs, memristor-based non-volatile solid-state memory, etc.), unalterable memory (e.g., EPROMs), read-only memory, and/or high-capacity storage devices (e.g., hard drives, solid state drives, etc.). In some examples, the memory 614 includes multiple kinds of memory, particularly volatile memory and non-volatile memory.

The memory 614 is computer readable media on which one or more sets of instructions, such as the software for operating the methods of the present disclosure, can be embedded. The instructions may embody one or more of the methods or logic as described herein. For example, the instructions reside completely, or at least partially, within any one or more of the memory 614, the computer readable medium, and/or within the processor 612 during execution of the instructions.

The terms "non-transitory computer-readable medium" and "computer-readable medium" include a single medium or multiple media, such as a centralized or distributed database, and/or associated caches and servers that store one or more sets of instructions. Further, the terms "non-transitory computer-readable medium" and "computer-readable medium" include any tangible medium that is capable of storing, encoding or carrying a set of instructions for execution by a processor or that cause a system to perform any one or more of the methods or operations disclosed herein. As used herein, the term "computer readable medium" is expressly defined to include any type of computer readable storage device and/or storage disk and to exclude propagating signals.

The sensors 604 are arranged in and/or around the vehicle 100 to monitor properties of the vehicle 100 and/or an environment in which the vehicle 100 is located. One or more of the sensors 604 may be mounted to measure properties around an exterior of the vehicle 100. Additionally or alternatively, one or more of the sensors 604 may be mounted inside a cabin of the vehicle 100 or in a body of the vehicle 100 (e.g., an engine compartment, wheel wells, etc.) to measure properties in an interior of the vehicle 100. For example, the sensors 604 include accelerometers, odometers, tachometers, pitch and yaw sensors, wheel speed sensors, microphones, tire pressure sensors, biometric sensors, and/or sensors of any other suitable type.

In the illustrated example, the sensors 604 include the range-detection sensors 102, the camera 210, the capacitive sensors 302, a seat occupancy sensor 616, a seatbelt sensor 618, and a thermometer 620. For example, the range-detection sensors 102 are configured to collect data to facilitate the autonomy unit 106 in performing autonomous driving maneuvers. The camera 210 and the capacitive sensors 302 are configured to detect a heart rate of the operator 204. Further, the seat occupancy sensor 616, the seatbelt sensor 618, and/or the thermometer 620 is configured to detect a heart rate of the operator 204. For example, the seat occupancy sensor 616 is sensor, such as a pressure sensor, that is configured to detect when the operator 204 is seated on the seat 202. The seatbelt sensor 618 is a sensor, such as a Hall-effect sensor, that is configured when a seatbelt of seat 202 is buckled. In the illustrated example, the seat occupancy sensor 616 and/or the seatbelt sensor 618 is configured to detect the heart rate of the operator 204 when the operator 204 is in contact with the seat 202 and/or the seatbelt, respectively. Further, the thermometer 620 of the illustrated example is configured to detect the heartrate of the operator 204 by monitoring a temperature of the operator 204 and/or a portion of the cabin 200 in which the operator 204 is located.

The HMI unit 606 provides an interface between the vehicle 100 and the operator 204. The HMI unit 606 includes digital and/or analog interfaces (e.g., input devices and output devices) to receive input from and display information for the operator 204. The input devices include, for example, the console input devices 208 and/or other input device(s), such as a control knob, an instrument panel, a touchscreen (e.g., the display 206), an audio input device (e.g., cabin microphone), buttons, or a touchpad. The output devices may include instrument cluster outputs (e.g., dials, lighting devices), actuators, the display 206 (e.g., a heads-up display, a center console display such as a liquid crystal display (LCD), an organic light emitting diode (OLED) display, a flat panel display, a solid state display, etc.), and/or speakers 622. For example, the display 206 is configured to emit a visual alert and/or one or more of the speakers 622 is configured to emit an audio alert to the operator 204 when the user-engagement controller 108 detects that the operator 204 is not grasping the steering wheel 300. In the illustrated example, the HMI unit 606 includes hardware (e.g., a processor or controller, memory, storage, etc.) and software (e.g., an operating system, etc.) for an infotainment system (such as SYNC® and MyFord Touch® by Ford®). Additionally, the HMI unit 606 displays the infotainment system on, for example, the display 206.

The ECUs 608 monitor and control the subsystems of the vehicle 100. For example, the ECUs 608 are discrete sets of electronics that include their own circuit(s) (e.g., integrated circuits, microprocessors, memory, storage, etc.) and firmware, sensors, actuators, and/or mounting hardware. The ECUs 608 communicate and exchange information via a vehicle data bus (e.g., the vehicle data bus 610). Additionally, the ECUs 608 may communicate properties (e.g., status of the ECUs 608, sensor readings, control state, error and diagnostic codes, etc.) to and/or receive requests from each other. For example, the vehicle 100 may have dozens of the ECUs 608 that are positioned in various locations around the vehicle 100 and are communicatively coupled by the vehicle data bus 610.

In the illustrated example, the ECUs 608 include the autonomy unit 106 and a body control module 624. The autonomy unit 106 controls performance of autonomous and/or semi-autonomous driving maneuvers of the vehicle 100 based upon, at least in part, data collected by the range-detection sensors 102 of the vehicle 100. The body control module 624 controls one or more subsystems throughout the vehicle 100, such as power windows, power locks, an immobilizer system, power mirrors, etc. For example, the body control module 624 includes circuits that drive one or more of relays (e.g., to control wiper fluid, etc.), brushed direct current (DC) motors (e.g., to control power seats, power locks, power windows, wipers, etc.), stepper motors, LEDs, etc.

The vehicle data bus 610 communicatively couples the communication module 104, the onboard computing platform 602, the sensors 604, the HMI unit 606, and the ECUs 608. In some examples, the vehicle data bus 610 includes one or more data buses. The vehicle data bus 610 may be implemented in accordance with a controller area network (CAN) bus protocol as defined by International Standards Organization (ISO) 11898-1, a Media Oriented Systems Transport (MOST) bus protocol, a CAN flexible data (CAN-FD) bus protocol (ISO 11898-7) and/a K-line bus protocol (ISO 9141 and ISO 14230-1), and/or an Ethernet™ bus protocol IEEE 802.3 (2002 onwards), etc.

Figure 7:
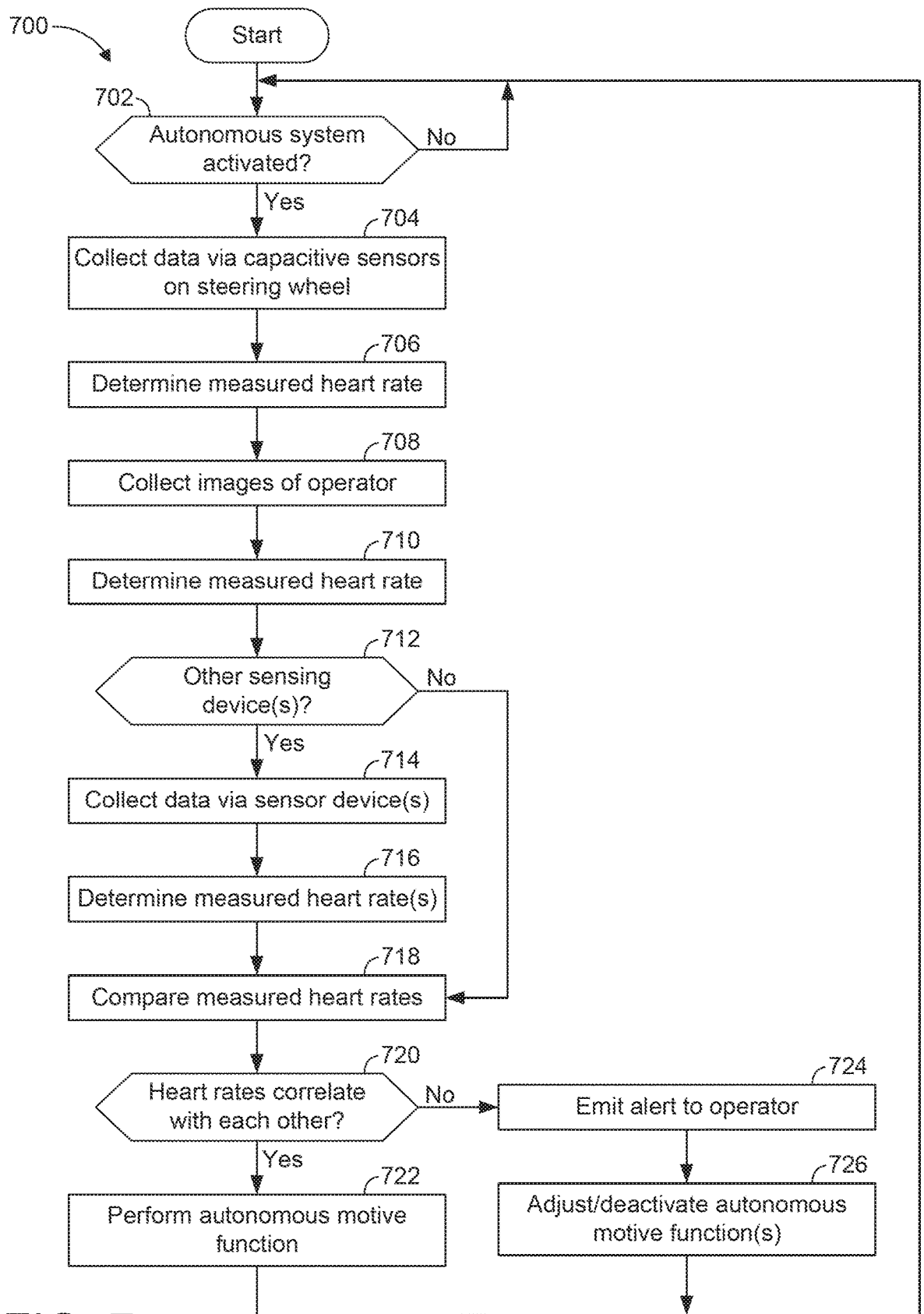
FIG. 7 is a flowchart for monitoring engagement with a steering wheel of a autonomous vehicle in accordance with the teachings herein.

FIG. 7 is a flowchart of an example method 700 to monitor an operator's engagement with a steering wheel of an autonomous vehicle. The flowchart of FIG. 7 is representative of machine readable instructions that are stored in memory (such as the memory 614 of FIG. 6) and include one or more programs which, when executed by a processor (such as the processor 612 of FIG. 6), cause the vehicle 100 to implement the example user-engagement controller 108 of FIGS. 1 and 6. While the example program is described with reference to the flowchart illustrated in FIG. 6, many other methods of implementing the example user-engagement controller 108 may alternatively be used. For example, the order of execution of the blocks may be rearranged, changed, eliminated, and/or combined to perform the method 700. Further, because the method 700 is disclosed in connection with the components of FIGS. 1-6, some functions of those components will not be described in detail below.

Initially, at block 702, the user-engagement controller 108 determines whether an autonomous system of the vehicle 100 is activated. For example, the user-engagement controller 108 detects whether a fully autonomous setting of the vehicle 100 has been activated by the operator 204. In response to the user-engagement controller 108 determining that an autonomous system is not active, the method 700 remains at block 702. Otherwise, in response to the user-engagement controller 108 determining that an autonomous system is active, the method 700 proceeds to block 704.

At block 704, the capacitive sensors 302 located on the steering wheel 300 collect data (e.g., capacitive and/or voltage measurements). At block 706, the user-engagement controller 108 determines a first measured heart rate based on the collected by the capacitive sensors 302. For example, the user-engagement controller 108 detects a rate at which the measurements spike over time determines the first measured heart rate based on the rate of measurement spikes. At block 708, the camera 210 captures images of the operator 204. At block 710, the user-engagement controller 108 determines a second measured heart rate based on the images captured by the camera 210. For example, the user-engagement controller 108 detects a characteristic that correlates with a measured heart rate of the operator 204 and within the captured images and determines the second measured heart rate based on the detected characteristic.

At block 712, the user-engagement controller 108 determines whether there are other sensing device(s) for measuring a heart rate of the operator 204. For example, the user-engagement controller 108 determines whether the seat occupancy sensor 616, the seatbelt sensor 618, the thermometer 620, a mobile device (e.g., a wearable, etc.) in communication with the communication module 104, and/or any other sensing device is able to measure a heart rate of the operator 204. In response to the user-engagement controller 108 determining that there is not another such sensing device, the method 700 proceeds to block 718. Otherwise, in response to the user-engagement controller 108 determining that there is one or more other such sensing devices, the method 700 proceeds to block 714 at which those sensing device(s) collect data and the user-engagement controller 108 collects the collected data from those sensing device(s). At block 716, the user-engagement controller 108 determines one or more measured heart rates based on the data collected at block 714.

At block 718, the user-engagement controller 108 compares the measured heart rates. For example, the user-engagement controller 108 compares the first measured heart rate, the second measured heart rate, and/or any other measured heart rates. At block 720, based on the comparison, the user-engagement controller 108 determines whether the measured heart rates correlate with each other. For example, the user-engagement controller 108 identifies that (1) the operator 204 is holding the steering wheel 300 if the measured heart rates correlate with each other, (2) the engagement-imitating device 400 is coupled to the steering wheel 300 if the measured hear rates do not correlate with each other, and/or (3) the operator 204 is not holding and the engagement-imitating device 400 is not coupled to the steering wheel 300 if the sensing device(s) (e.g., the camera 210, the capacitive sensors 302, etc.) do not detect a heart rate of the operator 204.

In response to the user-engagement controller 108 determining that the measured heart rates correlate with each other, the method 700 proceeds to block 722 at which the autonomy unit 106 performs autonomous motive function(s) for the vehicle 100. Otherwise, in response to the user-engagement controller 108 determining that one or more of the measured heart rates do correlate with the other(s), the method 700 proceeds to block 724 at which the user-engagement controller 108 emits an alert (e.g., an audio, visual, and/or haptic alert) to the operator 204. At block 726, the autonomy unit 106 adjusts and/or temporarily deactivates autonomous motive function(s) of the vehicle 100. For example, the autonomy unit 106 autonomously decelerates the vehicle 100 and/or temporarily disables performance of autonomous motive functions for the vehicle 100 until the user-engagement controller 108 detects that the operator 204 is holding the steering wheel 300 and the engagement-imitating device 400 is decoupled from the steering wheel 300.

In this application, the use of the disjunctive is intended to include the conjunctive. The use of definite or indefinite articles is not intended to indicate cardinality. In particular, a reference to "the" object or "a" and "an" object is intended to denote also one of a possible plurality of such objects. Further, the conjunction "or" may be used to convey features that are simultaneously present instead of mutually exclusive alternatives. In other words, the conjunction "or" should be understood to include "and/or". The terms "includes," "including," and "include" are inclusive and have the same scope as "comprises," "comprising," and "comprise" respectively. Additionally, as used herein, the terms "module" and "unit" refer to hardware with circuitry to provide communication, control and/or monitoring capabilities. A "module" and a "unit" may also include firmware that executes on the circuitry.

The above-described embodiments, and particularly any "preferred" embodiments, are possible examples of implementations and merely set forth for a clear understanding of the principles of the invention. Many variations and modifications may be made to the above-described embodiment(s) without substantially departing from the spirit and principles of the techniques described herein. All modifications are intended to be included herein within the scope of this disclosure and protected by the following claims.

What is claimed is:

1. A vehicle comprising:
    an autonomy unit configured to perform autonomous motive functions;
    a steering wheel;
    capacitive sensors coupled to the steering wheel;
    a second sensor configured to monitor an operator; and
    an onboard computing platform including a processor configured to:
        detect a first heart rate via the capacitive sensors;
        detect a second heart rate via the second sensor;
        identify that an engagement-imitating device is coupled to the steering wheel responsive to determining that the first heart rate does not correlate with the second heart rate; and
        emit an alert responsive to determining that the engagement-imitating device is coupled to the steering wheel.

2. The vehicle of claim 1, wherein the autonomy unit is configured to autonomously decelerate the vehicle responsive to the processor identifying that the engagement-imitating device is coupled to the steering wheel.

3. The vehicle of claim 1, wherein the processor is configured to disable the autonomy unit responsive to the processor identifying that the engagement-imitating device is coupled to the steering wheel.

4. The vehicle of claim 1, wherein the processor is configured to identify that the operator is holding the steering wheel responsive to determining that the first heart rate correlates with the second heart rate.

5. The vehicle of claim 1, wherein the processor is configured to enable the autonomy unit to perform the autonomous motive functions responsive to the processor identifying that the operator is holding the steering wheel without the engagement-imitating device being coupled to the steering wheel.

6. The vehicle of claim 1, wherein the processor is configured to identify that the operator is not holding the steering wheel when the processor does not detect the first heart rate and the second heart rate.

7. The vehicle of claim 6, wherein, responsive to identifying that the operator is not holding the steering wheel, the processor is configured to at least one of emit an alert, disable the autonomy unit, and decelerate the vehicle via the autonomy unit.

8. The vehicle of claim 1, further including a display, wherein the alert includes a visual alert and the processor is configured to emit the visual alert via the display.

9. The vehicle of claim 1, further including a speaker, wherein the alert includes an audio alert and the processor is configured to emit the audio alert via the speaker.

10. The vehicle of claim 1, further including a third sensor for monitoring a third heart rate of the operator.

11. The vehicle of claim 10, wherein the processor is configured to identify that the engagement-imitating device is coupled to the steering wheel responsive to determining that the third heart rate does not correlate with at least one of the first heart rate and the second heart rate.

12. The vehicle of claim 10, wherein the third sensor includes at least one of a seat occupancy sensor, a seatbelt sensor, a thermometer, and a capacitive touchscreen.

13. The vehicle of claim 1, further including a communication module configured to collect a third heart rate from a mobile device of the operator.

14. The vehicle of claim 13, wherein the processor is configured to identify that the engagement-imitating device is coupled to the steering wheel responsive to determining that the third heart rate does not correlate with at least one of the first heart rate and the second heart rate.

15. The vehicle of claim 1, wherein the second sensor includes a camera.

16. The vehicle of claim 1, wherein to detect the first heart rate:
one or more of the capacitive sensors is configured to collect measurements when the operator touches the steering wheel; and
the processor is configured to detect a rate at which the measurements spike and that correlates with a heart rate of the operator.

17. The vehicle of claim 1, wherein to detect the second heart rate, the processor is configured to detect a characteristic that correlates with a heart rate of the operator within images of the operator captured by the second sensor.

18. The vehicle of claim 1, wherein the processor is configured to determine that the first heart rate does not correlate with the second heart rate in response to determining that a difference between the first heart rate and the second heart rate is greater than a predefined threshold.

19. The vehicle of claim 1, wherein the processor is configured to normalize, filter, and align the first heart rate and the second heart rate prior to comparing the first heart rate and the second heart rate.

20. A method for an autonomous vehicle system, the method comprising:
detecting a first heart rate for an operator of a vehicle via capacitive sensors coupled to a steering wheel of the vehicle;
detecting a second heart rate for the operator via a camera of the vehicle;
comparing, via a processor of an onboard computing platform, the first heart rate and the second heart rate;
identifying, via the processor of the onboard computing platform, that an engagement-imitating device is coupled to the steering wheel responsive to determining that the first heart rate does not correlate with the second heart rate; and
emitting an alert responsive to determining that the engagement-imitating device is coupled to the steering wheel.

* * * * *